US012575977B2

(12) United States Patent

Saito

(10) Patent No.: US 12,575,977 B2

(45) Date of Patent: Mar. 17, 2026

(54) COMPOSITION FOR WET INDICATOR

(71) Applicant: HENKEL AG & CO., KGaA, Duesseldorf (DE)

(72) Inventor: Shigekazu Saito, Minoo (JP)

(73) Assignee: HENKEL AG & CO. KGaA, Duesseldorf (DE)

( * ) Notice: Subject to any disclaimer, the term of this patent is extended or adjusted under 35 U.S.C. 154(b) by 460 days.

(21) Appl. No.: 18/160,453

(22) Filed: Jan. 27, 2023

(65) Prior Publication Data

US 2023/0165731 A1 Jun. 1, 2023

Related U.S. Application Data

(63) Continuation of application No. PCT/JP2021/026606, filed on Jul. 15, 2021.

(30) Foreign Application Priority Data

Jul. 30, 2020 (JP) ................................. 2020-129592

(51) Int. Cl.
*A61F 13/42* (2006.01)
(52) U.S. Cl.
CPC ........ *A61F 13/42* (2013.01); *A61F 2013/422* (2013.01); *A61F 2013/427* (2013.01); *A61F 2013/428* (2013.01)
(58) Field of Classification Search
CPC ................ A61F 13/42; A61F 2013/422; A61F 2013/426; A61F 2013/427; A61F 2013/429
See application file for complete search history.

(56) References Cited

U.S. PATENT DOCUMENTS

| | | | | |
|---|---|---|---|---|
| 6,653,522 | B1 * | 11/2003 | Blumenthal | A61F 13/42 604/389 |
| 8,061,292 | B2 | 11/2011 | Ahmed et al. | |

| | | | | |
|---|---|---|---|---|
| 9,320,825 | B2 * | 4/2016 | Joseph | C09D 11/50 |
| 9,789,009 | B2 * | 10/2017 | Joseph | A61F 13/5323 |
| 10,383,972 | B2 | 8/2019 | Gu et al. | |
| 10,953,129 | B2 | 3/2021 | Corzani et al. | |
| 2016/0038628 | A1 * | 2/2016 | Klofta | A61L 15/26 436/39 |
| 2016/0303275 | A1 | 10/2016 | Joseph et al. | |
| 2022/0388269 | A1 * | 12/2022 | Bridewell | B32B 7/022 |

FOREIGN PATENT DOCUMENTS

| | | |
|---|---|---|
| CN | 107921171 A | 4/2018 |
| EP | 1940479 B1 | 2/2011 |
| JP | 2009511673 A | 3/2009 |
| JP | 2018515165 A | 6/2018 |
| JP | 2018517894 A | 7/2018 |
| WO | 2007044569 A3 | 4/2007 |
| WO | 2016166592 A1 | 10/2016 |

OTHER PUBLICATIONS

PCT International Search Report—PCT/JP2021/026606—Completed: Oct. 8, 2021 Mailing date: Oct. 20, 2021—Number of pp. 44.

Adhesives & Their Applications, Compiled by Huang Shiqiang, Sun Zhengguang, Wu Jun, Machinery Industry Press, Dec. 2011, pp. 228-231.

* cited by examiner

*Primary Examiner* — Catharine L Anderson

(74) *Attorney, Agent, or Firm* — Sun Hee Thomas

(57) ABSTRACT

To provide a composition for wet indicator which is excellent in discoloration performance and is suppressed in odor. What is disclosed is a composition for wet indicator comprising: a hydrocarbon oil (A), at least one selected from saturated fatty acids having 16 or more carbon atoms and derivatives thereof (B), and a wet-sensitive colorant composition (C), wherein the component (B) is contained in an amount of 2 to 85 parts by mass based on 100 parts by mass of the total amount of the components (A) to (C).

19 Claims, No Drawings

COMPOSITION FOR WET INDICATOR

CROSS-REFERENCE TO RELATED APPLICATION

This application is a continuation of International Application No. PCT/JP2021/026606, filed Jul. 15, 2021, claims benefit under Article 4 of the Paris Convention based on Japanese Patent Application No. 2020-129592 filed in Japan on Jul. 30, 2020, incorporated herein by reference in its entirety.

TECHNICAL FIELD

The present invention relates to a wet indicator which is a member that notifies the presence of moisture by discoloration.

BACKGROUND ART

Examples of an article that exhibits a function by being in contact with moisture include a moisture exchanger (HEM), a moisture detector, an autoclave (sterilization) tape, a packaging article and an absorbent article. As a device that displays that these articles are in a wet state and exhibit a function, a wet indicator is known. Wetting refers to a state in which a liquid comprising water such as a body fluid, that is, moisture is in contact. The indicator refers to a display tool and a marking tool.

Generally, the wet indicator changes its color to indicate whether the article is dry or wet with moisture. For example, the wet indicator is colored or discolored when the article is wet, thereby displaying a status of wet state of the article.

Patent Documents 1 to 3 describe a composition for wet indicator used in combination with an absorbent article such as a diaper.

Patent Document 1 describes a wet indicator composition that changes color in response to pH change. The wet indicator composition contains a water-insoluble thermoplastic polymer composition, a superabsorbent polymer, a wet indicator and a surfactant. ([Abstract], [Claim 1], [Claim 2]).

Patent Document 2 describes a hot melt damp indicator composition that may be applied using a conventional hot melt applicator device. This hot melt damp indicator composition contains components such as a water-insoluble thermoplastic polymer, an anionic surfactant and a leuco dye ([Abstract], [Claim 1], [0006]).

Patent Document 3 describes a dampness/fluid indicator composition that is colorless in its initial state and may provide various final wet color options in the presence of water. The dampness/fluid indicator composition includes a leuco dye and a color-developing agent in a hot melt adhesive matrix ([Abstract], [0001], [0008]).

PRIOR ART DOCUMENTS

Patent Documents

Patent Document 1: JP 2009-511673 A

Patent Document 2: JP 2018-515165 A

Patent Document 3: JP 2018-517894 A

SUMMARY OF THE INVENTION

Problems to be Solved by the Invention

However, in a conventional composition for wet indicator, a matrix, that is, a main continuous phase is composed of a thermoplastic resin and permeability of moisture is not sufficiently excellent. Such a conventional composition for wet indicator has a weak degree of discoloration when brought into contact with moisture, and timing of discoloration can be delayed, thus there is still a room for improvement in discoloration performance. In addition, the conventional wet indicator has an odor, which causes an unpleasant feeling to a user, and also has a problem that the odor is transferred to an absorbent article.

The present invention solves such problems, and an object thereof is to provide a composition for wet indicator which is excellent in discoloration performance and is suppressed in odor.

Means for Solving the Problems

The present invention provides a composition for wet indicator comprising: a hydrocarbon oil (A), at least one selected from saturated fatty acids having 16 or more carbon atoms and derivatives thereof (B), and a wet-sensitive colorant composition (C), wherein the component (B) is contained in an amount of 2 to 85 parts by mass based on 100 parts by mass of the total amount of the components (A) to (C).

In an embodiment, the component (B) contains at least one selected from 12-hydroxystearic acid and metal salts of the 12-hydroxystearic acid.

In an embodiment, the component (C) is a composition comprising a leuco dye or a pH indicator and an anionic surfactant or a nonionic surfactant.

In an embodiment, the anionic surfactant contains a linear alkylbenzene sulfonate.

Also, the present invention provides a wet indicator having the composition for wet indicator according to any of the above.

Also, the present invention provides an absorbent article having the above wet indicator.

Effects of the Invention

According to the present invention, a composition for wet indicator which is excellent in discoloration performance and is suppressed in odor is provided.

Embodiment of the Invention (A) Hydrocarbon Oil

The hydrocarbon oil contained in the composition for wet indicator of the present invention refers to a lipophilic hydrocarbon compound that is liquid at room temperature. For example, wax is a hydrocarbon compound but is solid at room temperature and thus does not correspond to a hydrocarbon oil. Since a solid hydrocarbon substance is poor in water permeability, when used in a matrix of the composition for wet indicator, it is likely to adversely affect discoloration properties of the composition for wet indicator.

The hydrocarbon oil preferably contains at least one selected from paraffin oil, naphthene oil and aromatic oils, from the viewpoint of improving compatibility with a colorant. The hydrocarbon oil more preferably contains at least one selected from paraffin oil and naphthene oil, and even more preferably contains paraffin oil. Weight average molecular weight of the hydrocarbon oil is preferably from 200 to 2000, from the viewpoint of improving water permeability.

As the hydrocarbon oil, a commercially available product may be used. Examples of the commercially available hydrocarbon oil include White Oil Broom 350 (trade name) manufactured by Kukdong Oil & Chemicals Co., Ltd., Diana Fresia PW32 (trade name), Diana Process Oil PW-90 (trade name) and Daphne Oil KP-68 (trade name) manufactured by Idemitsu Kosan Co., Ltd., Nyflex 222B (trade name) manufactured by Nynas AB, SUNPURE N90 manufactured by JAPAN SUN OIL COMPANY, LTD., KN4010 (trade name) manufactured by PetroChina Company Limited, Enerper M1930 (trade name) manufactured by BP Chemicals Ltd., Kaydol (trade name) manufactured by Crompton Corporation and Primol 352 (trade name) manufactured by Esso Standard Oil.

The hydrocarbon oil is contained in the composition for wet indicator in an amount of 5 to 90 parts by mass, preferably from 20 to 75 parts by mass, and more preferably from 30 to 65 parts by mass, based on 100 parts by mass of the total amount of the hydrocarbon oil and the saturated fatty acid and the wet-sensitive colorant composition, namely the components (A) to (C). By adjusting the content of the hydrocarbon oil in the composition for wet indicator within the above ranges, compatibility between the hydrocarbon oil and the colorant is improved and protons are easily generated, and the composition for wet indicator of the present invention may exhibit clear and rapid coloration.

(B) Saturated Fatty Acid

The saturated fatty acid refers to a fatty acid having no double bond or triple bond in the carbon chain. The fatty acid is an aliphatic carboxylic acid having at least one carboxyl group.

The saturated fatty acid contained in the composition for indicator of the present invention has a property of making the entire composition to gel by crosslinking. A saturated fatty acid having a hydroxyl group is preferable because it is easily crosslinked. The saturated fatty acid is preferably in the form of a chain. Moreover, the chain saturated fatty acid is preferably a linear saturated fatty acid. The saturated fatty acid is crosslinked in the presence of the hydrocarbon oil, whereby the hydrocarbon oil is contained in the crosslinked saturated fatty acid. The saturated fatty acid used may be a known substance. Such saturated fatty acids are preferably saturated fatty acids having 16 or more carbon atoms and derivatives thereof, from the viewpoint of improving water permeability.

The composition for wet indicator of the present invention comprises an oily gel by the hydrocarbon oil being contained in the three-dimensionally crosslinked saturated fatty acid. The composition for wet indicator, which contains an oily gel, has moderate hardness that is softer than that of a hot-melt type composition for wet indicator, and moisture so easily penetrates into the composition, that the composition is strongly and quickly discolored. Thereby, with the wet indicator of the present invention, a status of wet state of the article may be accurately displayed. In addition, since the oily gel is able to contain a colorant or a body fluid that causes odor, it is possible to reduce the odor of the absorbent article of the present invention.

The saturated fatty acid has more preferably from 16 to 36 carbon atoms, and further preferably from 18 to 20 carbon atoms. Specific examples of the saturated fatty acid having 16 or more carbon atoms include arachidic acid having 20 carbon atoms, stearic acid having 18 carbon atoms, 12-hydroxystearic acid having 18 carbon atoms, margaric acid having 17 carbon atoms, palmitic acid having 16 carbon atoms and 16-hydroxyhexadecanoic acid having 16 carbon atoms. Among them, 12-hydroxystearic acid is particularly preferable.

The saturated fatty acid derivative refers to a compound in which a part of the saturated fatty acid is substituted with a coexisting group. The saturated fatty acid derivative may have from 16 or more carbon atoms, preferably from 16 to 36 carbon atoms, and more preferably from 18 to 20 carbon atoms. For example, a fatty acid amide, fatty acid alkyl ester, fatty acid metal salt, monoglyceride, diglyceride, sorbitan fatty acid ester or diglycerin fatty acid ester having 16 or more carbon atoms may be used as the saturated fatty acid derivative. Preferred saturated fatty acid derivatives include saturated fatty acid metal salts.

The saturated fatty acid derivative particularly preferably has a chemical structure derived from stearic acid. The "chemical structure derived from stearic acid" refers to the unit represented by formula $$CH_3(CH_2)_{16}COOH \tag{1}$$

The saturated fatty acid derivative also includes a chemical structure in which a part of formula (1) is substituted with another coexisting group (for example, a hydroxyl group, an alkyl group, an alkali metal, or an alkaline earth metal) and an oligomer or a polymer having the unit represented by formula (1).

The fatty acid metal salt is preferably a metal salt having a chemical structure derived from stearic acid, and specific examples thereof include sodium stearate and lithium 12-hydroxystearate having 18 carbon atoms, and magnesium stearate having 36 carbon atoms. Among them, lithium 12-hydroxystearate is particularly preferable.

When the composition for wet indicator of the present invention contains 12-hydroxystearic acid and lithium 12-hydroxystearate, three-dimensional crosslinking so easily occurs, which easily contains the hydrocarbon oil, that it is easy to prepare an oily gel having appropriate hardness. When the oily gel is formed to have appropriate hardness, moisture easily penetrates into the gel. As the moisture easily permeates, the moisture and the surfactant easily coexist, generation of protons is facilitated, and discoloration of the colorant is promoted.

The saturated fatty acid is blended with the hydrocarbon oil to form a continuous porous body like tissue, and forms a structure in which the hydrocarbon oil is confined in voids of the continuous porous body. By blending the hydrocarbon oil with the saturated fatty acid, an oily gel having appropriate hardness is obtained, and the oily gel has a fine continuous porous body. In the composition for wet indicator of the present invention, since the oily gel has a fine continuous porous structure, for example, moisture such as urine and body fluid is possible to easily permeate therein.

The saturated fatty acid is contained in the composition for wet indicator in an amount of from 2 to 85 parts by mass, preferably from 10 to 70 parts by mass, and more preferably from 20 to 60 parts by mass, based on 100 parts by mass of the total amount of the hydrocarbon oil, the saturated fatty acid and the wet-sensitive colorant composition, namely the components (A) to (C). By adjusting the content of the saturated fatty acid in the composition for wet indicator within the above ranges, compatibility between the hydrocarbon oil and the colorant is improved and protons are easily generated, and the composition for wet indicator of the present invention may exhibit clear and rapid coloration.

(C) Wet-Sensitive Colorant Composition

The composition for wet indicator of the present invention comprises a wet-sensitive colorant composition. The wet-sensitive colorant composition refers to a composition comprising a colorant that is substantially discolored when receiving protons and a surfactant that releases protons in the presence of water. As the colorant and the surfactant used in the wet-sensitive colorant composition, known colorants and surfactants may be used in combination.

The colorant includes a dye, an indicator and a pigment. Specific examples of the colorant that may be used include oxazolidine-based dyes, azo-based dyes, methine-based dyes, anthraquinone-based dyes and leuco dyes. The colorant preferably contains a leuco dye and a pH indicator, from the viewpoint of obtaining rapid and clear discoloration. Since the leuco dye or the pH indicator has strong proton sensitivity, use of the leuco dye or the pH indicator improves discoloration performance of the composition for wet indicator.

The leuco dye is a dye that may change between two chemical species (one of which is colorless). Reversible transformations are caused by heat, light or pH; resulting in examples of thermochromism, photochromism and halochromism, respectively. Typical irreversible transformations are caused by reduction or oxidation. The colorless form is sometimes referred to as a leuco form.

The leuco dye is not limited as long as it is sufficiently colored, and a known or commercially available one may be used. For example, the following compounds such as a leuco dye that may develop color by an acid may be suitably used. These may be used singly or in two or more kinds thereof.

(a) Fluorans: 2'-[(2-chlorophenyl)amino]-6'-(dibutylamino)-spiro[isobenzofuran-1(3H),9'-(9H)xanthen]-3-one, 3-diethylamino-6-methyl-7-chlorofluoran, 3-dimethylaminobenzo(a)-fluoran, 3-amino-5-methylfluoran, 2-methyl-3-amino-6,7-dimethylfluoran, 2-bromo-6-cyclohexylaminofluoran, 6'-ethyl(4-methylphenyl)amino-2'-(N-methylphenylamino)-spiro(isobenzofuran1(3H),9'-(9H)xanthen)-3-one, 3,6-diphenylaminofluoran, 9-ethyl(3-methylbutyl)amino-spiro[12H-benzo(a)xanthene-12,1'(3'H)isobenzofuran]-3'-one and 2'-[bis(phenylmethyl)amino]-6'-(diethylamino)-spiro-[isobenzofuran-1(3H),9'-(9H)xanthen]-3-one;

(b) Fluorens: 3,6-bis(diethylamino)fluorenespiro(9,3')-4'-azaphthalide and 3,6-bis(diethylamino)fluorenespiro(9,3')-4',7'-diazaphthalide;

(c) Diphenylmethane phthalides: 3,3-bis-(p-ethoxy-4-dimethylaminophenyl)phthalide;

(d) Diphenylmethane azaphthalides: 3,3-bis-(1-ethoxy-4-diethylaminophenyl)-4-azaphthalide and 3,3-bis(4-diethyl-amino-2-ethoxyphenyl)-4-azaphthalide;

(e) Indolyl phthalides: 3,3-bis(n-butyl-2-methylindol-3-yl)phthalide and 3,3-bis(1-ethyl-2-methylindol-3-yl)phthalide;

(f) Phenylindolyl phthalides: 3-(1-diethylaminophenyl)-3-(1-ethyl-2-methylindol-3-yl)phthalide;

(g) Phenylindolyl azaphthalides: 3-(2-ethoxy-4-diethylaminophenyl)-3-(1-ethyl-2-methylindol-3-yl)-4-azaphthalide and 3-[2-ethoxy-4-(N-ethylanilino)phenyl]-3-(1-ethyl-2-methylindol-3-yl)-4-azaphthalide;

(h) Styrylquinolines: 2-(3-methoxy-4-dodecoxystyryl)quinoline;

(i) Diazarhodamine lactones: 2-(dimethylamino)-8-(dimethylamino)-4-methyl-spiro[5H-(1)benzopyrano(2,3-d)pyrimidine-5,1'(3'H)-isobenzofuran];

(j) Pyridines: 2,6-diphenyl-4-(6-dimethylaminophenyl)pyridine and 2,6-diethoxy-4-(4-diethylaminophenyl)pyridine;

(k) Quinazolines: 2-(4-N-methylanilinophenyl)-1-phenoxyquinazoline and 2-(4-dimethylaminophenyl)-4-(1-methoxyphenyloxy)quinazoline;

(l) Bisquinazolines: 4,4'-(ethylenedioxy)-bis[2-(1-diethylaminophenyl)quinazoline] and 4,4'-(ethylenedioxy)-bis[2-(1-di-n-butylaminophenyl)quinazoline];

(m) Ethylenophthalides: 3,3-bis[1,1-bis-(p-dimethylaminophenyl)ethyleno-3]phthalide;

(n) Ethylenoazaphthalides: 3,3-bis[1,1-bis-(p-dimethylaminophenyl)ethyleno-2]-4-azaphthalide and 3,3-bis[1,1-bis-(p-dimethylaminophenyl)ethyleno-2]-4,7-diazaphthalide;

(o) Aminophthalides: 3,3-bis(p-dimethylaminophenyl)-6-dimethylaminophthalide (crystal violet lactone).

In addition, at least one of aminophthalides and fluorans may be used as a colorant. As the fluoran, particularly, 2'-[bis(phenylmethyl)amino]-6'-(diethylamino)-spiro-[isobenzofuran-1(3H),9'-(9H)xanthen]-3-one, 2'-[(2-chlorophenyl)amino]-6'-(dibutylamino)-spiro[isobenzofuran-1(3H),9'-(9H)xanthen]-3-one and 3,6-diphenylaminofluoran are more preferable. As the aminophthalides, crystal violet lactone is particularly preferable.

When the composition for wet indicator of the present invention contains a leuco dye as a colorant, the leuco dye is easily ring-opened by protons generated in the presence of a surfactant and urine (moisture), and the composition for wet indicator is quickly colored, which is preferable. The content of the leuco dye may be appropriately determined according to the type of the leuco dye and a desired hue.

The pH indicator refers to a chemical to be added to a reaction liquid in order to know an equivalent point by a change directly visible, such as a change in color or formation of a precipitate in titration. As the pH indicator, an acid-base indicator is used. Specific examples of the pH indicator include phenolphthalein, methyl orange, potassium chromate, bromocresol green and bromophenol blue.

The colorant is contained in the composition for wet indicator in an amount of from 0.05 to 5 parts by mass, preferably from 0.1 to 3 parts by mass, and more preferably from 0.5 to 2 parts by mass, based on 100 parts by mass of the total amount of the hydrocarbon oil, the saturated fatty acid and the wet-sensitive colorant composition, namely the components (A) to (C). By adjusting the content of the colorant in the composition for wet indicator within the above ranges, color difference between the dry state and the wet state of the composition for wet indicator increases, and discoloration may be easily perceived.

The colorant is used in combination with a surfactant to be a wet-sensitive colorant composition. The surfactant improves compatibility of the colorant with other components, and the colorant is easily contained in the oily gel.

The surfactant is a substance exhibiting a function of discoloring the colorant in the presence of moisture. For example, anionic surfactants and nonionic surfactants are preferable because they are easily wetted with water to generate protons, and many colorants are discolored by receiving protons.

Examples of the anionic surfactant include:

alkali metal alkyl sulfates such as sodium dodecyl sulfate and potassium dodecyl sulfate; sodium dodecyl polyglycol ether sulfate;

ammonium alkyl sulfates such as ammonium dodecyl sulfate;

sodium sulfosinoate;

alkyl sulfonates such as alkali metal salts of sulfonated paraffin and ammonium salts of sulfonated paraffin;

fatty acid salts such as sodium laurate, triethanolamine oleate and triethanolamine abietate;

alkylaryl sulfonates such as sodium dodecylbenzene sulfonate and alkali metal sulfates of alkali phenol hydroxyethylene;

high alkyl naphthalene sulfonates;

naphthalenesulfonic acid formalin condensate;

dialkyl sulfosuccinates;

polyoxyethylene alkyl sulfate salts; and polyoxyethylene alkylaryl sulfate salts.

Examples of the nonionic surfactant include:

polyoxyethylene alkyl ethers;

polyoxyethylene alkylaryl ethers;

sorbitan fatty acid ester;

polyoxyethylene sorbitan fatty acid ester;

fatty acid monoglyceride such as glycerol monolaurate;

polyoxyethyleneoxypropylene copolymer; and condensation product of ethylene oxide and aliphatic amine, amide or acid.

The surfactant is preferably an anionic surfactant, more preferably a linear alkylbenzene sulfonate, and further preferably sodium dodecylbenzene sulfonate. When sodium dodecylbenzene sulfonate is used as the surfactant, the colorant is easily dissolved in the hydrocarbon oil, and the hydrocarbon oil is so easily brought into contact with water, that protons are easily generated. Since protons are easily provided to the colorant, discoloration of the composition for wet indicator rapidly proceeds.

The surfactant is contained in the composition for wet indicator in an amount of from 1 to 40 parts by mass, preferably from 3 to 30 parts by mass, and more preferably from 4 to 22 parts by mass, based on 100 parts by mass of the total amount of the hydrocarbon oil, the saturated fatty acid and the wet-sensitive colorant composition, namely the components (A) to (C). By adjusting the content of the surfactant in the composition for wet indicator within the above ranges, sensitivity of the composition for wet indicator to moisture is improved, and a wet state is accurately displayed.

Pigment

In the composition for wet indicator of the present invention, a pigment may be used as necessary. The pigment includes inorganic pigments and organic pigments. The inorganic pigment includes colored inorganic pigments and extender pigments.

Examples of the colored inorganic pigment include white titanium oxide, white lead (basic lead carbonate), zinc white (zinc oxide), lithopone (barium sulfate/zinc sulfide);

reddish red iron(III) oxide, red lead (lead oxide), silver vermilion (mercury sulfide), molybdenum-red;

yellowish chrome yellow (lead chromate), cadmium yellow (cadmium sulfide), zinc chromate, litharge (lead monoxide);

bluish ultramarine blue, prussian blue, cobalt blue (cobalt aluminate); and black pigment includes iron black (iron(II, III) oxide and carbon black.

Examples of the extender pigment include barite (barium sulfate), gypsum (hydrous calcium sulfate), kaolin (ceyssatite), silica (silicon dioxide), white carbon (precipitated silica), talc, barium carbonate and calcium carbonate.

Examples of the organic pigment include lake and colored organic pigments. There are two types of lake, one of which is dyeing lake, which is a pigment obtained by dyeing an extender pigment with a dye. Another lake is one in which a dye is made insoluble by reacting with a divalent or higher metal salt, and examples thereof include azo lake formed from an azo dye.

Examples of the colored organic pigment include insoluble azo pigments, metal phthalocyanine pigments, anthraquinone pigments and vat pigments. Among azo dyes, anthraquinone dyes and indigo dyes shown as representative types of dyes based on chemical structures, substances insoluble in water are used as pigments. Moreover, the metal phthalocyanine pigment has a color tone from blue to green, and is excellent in light resistance.

Tackifier Resin

In the composition for wet indicator of the present invention, a tackifier resin may be used as necessary. Examples of the tackifier resin include natural rosin, modified rosin, hydrogenated rosin, glycerol esters of natural rosin, glycerol esters of modified rosin, pentaerythritol esters of natural rosin, pentaerythritol esters of modified rosin, pentaerythritol esters of hydrogenated rosin, copolymers of natural terpenes, three-dimensional polymers of natural terpenes, hydrogenated derivatives of copolymers of hydrogenated terpenes, polyterpene resins, hydrogenated derivatives of phenol-based modified terpene resins, aliphatic petroleum hydrocarbon resins, hydrogenated derivatives of aliphatic petroleum hydrocarbon resins, aromatic petroleum hydrocarbon resins, hydrogenated derivatives of aromatic petroleum hydrocarbon resins, cyclic aliphatic petroleum hydrocarbon resins and hydrogenated derivatives of cyclic aliphatic petroleum hydrocarbon resins.

As the tackifier resin, a commercially available product may be used. Examples of such a commercially available product include KE-604 (trade name), ARKON P100 (trade name) and ARKON M100 (trade name) manufactured by Arakawa Chemical Industries, Ltd., RHR-101HK manufactured by Wuzhou Sun Shine Forestry & Chemicals Co., Ltd., Foral AX-E (trade name) manufactured by Eastman Chemical Company, FTR6100 manufactured by Mitsui Chemicals, Inc., CLEARON M105 (trade name) manufactured by YASUHARA CHEMICAL CO., LTD., ECR5600 (trade name) and ECR179EX (trade name) manufactured by Exxon Mobil Corporation and Quinton DX390 (trade name) manufactured by Zeon Corporation. These commercially available tackifier resins may be used alone or in combination.

In consideration of compatibility between the surfactant and the hydrocarbon oil, RHR-101HK and Foral AX-E, which are rosin-based tackifier resins, are particularly preferable as the tackifier resin.

Other Components

The composition for wet indicator of the present invention may contain, as components other than the above, at least one additive of a thickener (styrene-based polymer, olefin-based polymer), an antioxidant (phenol-based, phosphorus-based and sulfur-based), an ultraviolet absorber, a fluorescent brightening agent, a non-discoloring dye, a fragrance, a disinfectant, an antibacterial agent, a repellent, a skin care component, a non-discoloring pigment, a lubricant and a filler.

Method for Producing Composition for Wet Indicator

The composition for wet indicator of the present invention is prepared by mixing the above-described components with heating as necessary. When the components are mixed until they become uniform and cooled to room temperature, the composition for wet indicator gels and becomes hard.

For example, all the components contained in the composition for wet indicator are put into a container, and the components are dissolved or uniformly dispersed, and heated and stirred until a uniform state is obtained. The heating temperature is appropriately adjusted generally in the range of from 50 to 250° C., preferably from 70 to 200° C., and more preferably from 80 to 160° C. The heating time is determined in consideration of the heating temperature, but is generally adjusted between 5 minutes and 1 hour, and preferably between 10 minutes and 40 minutes. A uniform composition may be prepared by putting each component into a container in turn and sequentially mixing the components.

Wet Indicator

The composition for wet indicator is molded into a suitable shape and is used as a wet indicator, optionally in combination with a component, substance or material that does not impair wet indicator function. The composition for wet indicator may be used as a single material, for example, by being applied onto a substrate material such as a film or paper, or may be used in combination with a water-absorbent substance. The wet indicator of the present invention may be used for various articles in which a wet state needs to be detected, but is particularly preferably used for absorbent articles.

When the composition for wet indicator and the water-absorbent substance are combined, examples of embodiment thereof are as follows. That is, positioning a composition for wet indicator and a water-absorbent substance adjacent to each other; mixing the composition for wet indicator and the water-absorbent substance; and heating the composition for wet indicator and the water-absorbent substance to be compatible with each other.

The water-absorbent substance may be a known resin having a water-absorbing property such as polyvinyl alcohol or an acrylic resin or a known substance having a water-absorbing property such as wood, paper or cloth, and shape of the water-absorbent substance may be any shape such as a sheet shape, a lump shape, a granular shape or a fibrous shape.

Absorbent Article

The absorbent article of the present invention includes a water-absorbent substance and the composition for wet indicator of the present invention. Specifically, the absorbent article is a so-called hygienic material such as a sanitary napkin, a urine absorbing liner, puerperal shorts, a breast milk pad, an armpit sweat pad, a paper diaper, a pet sheet, a hospital gown and a surgical white gown.

The absorbent article is composed of at least one member selected from a group consisting of a woven fabric, a nonwoven fabric, a rubber, a resin, paper and a polyolefin film, and the wet indicator according to the present invention. The polyolefin film is preferably a polyethylene film for reasons such as durability and cost.

When the wet indicator of the present invention is used for paper diaper, the wet indicator is preferably attached to the surface of the powder or particles of the water-absorbent resin stored in the disposable diaper. In addition to the paper diaper, by applying the wet indicator of the present invention to a surface of various substrate materials such as resin particles, woven fabric, nonwoven fabric, resin sheet, paper, resin molded article, metal and wood by any means, a moisture wet indicator action may be provided on the surface of various substrate materials.

EXAMPLES

Hereinafter, for the purpose of describing the present invention in more detail and specifically, the present invention will be described using examples, but these examples do not limit the present invention at all.

In Examples and Comparative Examples, components to be blended in a composition for wet indicator are shown below.

Hydrocarbon Oils

Paraffin oil (liquid paraffin (trade name) manufactured by FUJIFILM Wako Pure Chemical Corporation)

Paraffin oil (Daphne Oil KP-68 (trade name) manufactured by Idemitsu Kosan Co., Ltd.)

Paraffin oil (Diana Fresia PW-32 (trade name) manufactured by Idemitsu Kosan Co., Ltd.)

Naphthenic oil (KNH4010 (trade name) manufactured by PetroChina Company Limited)

Liquid polybutene (Nisseki Polybutene HV-100 (trade name) manufactured by JXTG Nippon Oil & Energy Corporation)

Colorants constituting the wet-sensitive colorant composition are as follows.

Colorants pH Indicator (bromocresol green (trade name) manufactured by FUJIFILM Wako Pure Chemical Corporation)

Leuco dye (crystal violet lactone (trade name) manufactured by FUJIFILM Wako Pure Chemical Corporation)

Leuco dye (Blue 1 (trade name) manufactured by Yamada Chemical Co., Ltd.)

Leuco dye (Blue 203 (trade name) manufactured by Yamada Chemical Co., Ltd.)

Surfactants constituting the wet-sensitive colorant composition are as follows.

Surfactants

Anionic surfactant (sodium dodecylbenzene sulfonate (reagent name) manufactured by KANTO CHEMICAL CO., INC.)

Anionic surfactant (Aerosol QT-100 (trade name) manufactured by SOLVAY)

Nonionic surfactant (SURFLIC-AQ250 (trade name) manufactured by Itoh Oil Chemicals Co., Ltd.)

Saturated Fatty Acids having 16 or More Carbon Atoms or Derivatives Thereof

Saturated fatty acid having 16 carbon atoms (16-hydroxy-hexadecanoic acid (reagent name) manufactured by FUJIFILM Wako Pure Chemical Corporation)

Saturated fatty acid derivative having 36 carbon atoms (magnesium stearate (reagent name) manufactured by FUJIFILM Wako Pure Chemical Corporation)

Saturated fatty acid having 18 carbon atoms (12-hydroxystearic acid (reagent name) manufactured by FUJIFILM Wako Pure Chemical Corporation)

Saturated fatty acid derivative having 18 carbon atoms (sodium stearate (reagent name) manufactured by FUJIFILM Wako Pure Chemical Corporation)

Tackifier Resin

Hydrogenated rosin-based tackifier resin (RHR-101HK (trade name) manufactured by Wuzhou Sun Shine Forestry & Chemicals Co., Ltd.)

Hydrogenated rosin-based tackifier resin (Foral AX-E (trade name) manufactured by Eastman Chemical Japan Ltd.)

Hydrogenated hydrocarbon-based tackifier resin (HD-1100 (trade name) manufactured by Tiajin Luhua Chemical Co., Ltd.)

Hydrogenated hydrocarbon-based tackifier resin (ARKON P100 (trade name) manufactured by Arakawa Chemical Industries, Ltd.)

Hydrogenated hydrocarbon-based tackifier resin (ECR5400 (trade name) manufactured by Exxon Mobil Corporation)

Hydrogenated hydrocarbon-based tackifier resin (FTR-6100 (trade name) manufactured by Mitsui Chemicals, Inc.)

The above-described components were blended in ratios shown in Tables 1 to 4, and stirred and mixed to prepare a composition for wet indicator. Specifically, components were placed in a 70 ml container and heated to 130° C. with a glass-col heater, and a blend of the components was stirred using a stirrer at a stirring speed of from 300 to 500 rpm for 20 minutes. All numerical values relating to the composition for wet indicator (composition) shown in Tables 1 to 4 are parts by mass (solid content).

For the compositions for wet indicator of Examples and Comparative Examples, appearance was confirmed whether or not an oily gel was formed, and phase separation, odor, discoloration time and color bleeding were evaluated. Details of the evaluation are shown below.

Appearance

The compositions for wet indicator of Examples and Comparative Examples were allowed to stand at room temperature for 1 day, and appearance of each composition was visually observed to confirm whether or not an oily gel was generated.

Whether or not the composition for wet indicator was a gel was evaluated by fluidity of the composition and oozing-out of the oily substance.

The composition was placed in a container, the composition was not flowable even when the container was tilted, and a commercially available oil blotting paper was pressed against the composition, and when oil exudation was visually recognized, the composition was determined as a gel. The evaluation results are as shown in Tables 1 to 4.

Hardness of the composition for wet indicator was evaluated according to the following criteria. In an environment of 23° C., a cylindrical SUS probe was pressed against the composition for wet indicator of each of Examples and Comparative Examples to apply a load of 1 kg, and after 8 seconds, the degree of penetration of the SUS probe into the composition was confirmed to evaluate hardness of the composition. The evaluation criteria are as follows.

Penetration of probe having a diameter of 16 mm is 4 mm or more: Very soft

Penetration of probe having a diameter of 16 mm is less than 4 mm: Soft

Penetration of the probe having a diameter of 5 mm is less than 4 mm: Hard

Penetration of probe having a diameter of 3 mm is less than 4 mm: Very hard

Phase Separation

Using 30 g of the composition for wet indicator of each of Examples and Comparative Examples as an evaluation sample, 30 g of each sample was placed in a 70 ml glass container and allowed to stand in a heating furnace at 100° C. After aging the sample for 24 hours, the presence or absence of phase separation was visually confirmed to evaluate whether the composition was uniform or non-uniform.

A: No phase separation is observed, and no turbidity is observed

B: Phase separation is not observed and is uniform, but slight turbidity is observed C: A slightly transparent supernatant is observed at the top D: Obvious phase separation is observed Odor Using 30 g of the composition for wet indicator of each of Examples and Comparative Examples as an evaluation sample, 30 g of each sample was placed in a 70 ml glass container, covered with an aluminum foil, and then allowed to stand in a dryer at 40° C. for 1 hour. Thereafter, the container was taken out from the dryer, the aluminum foil was removed, and odor was confirmed. The evaluation criteria are as follows.

A: No odor is sensed

B: A slight odor is sensed

C: An obvious odor is sensed but is not unpleasant

D: A strong and unpleasant odor is sensed

Discoloration Test

The wet indicator composition of each of Examples and Comparative Examples was placed in a glass bottle, and the glass bottle was heated in a dryer at 100° C. until a uniform liquid was obtained. Subsequently, an appropriate amount of each composition was dropped on a hiding rate test paper (JIS K-5600, manufactured by TP Giken Co., Ltd.), then a uniform film having a thickness of about 27.5 μm was quickly prepared with a bar coater (No. 12 manufactured by Daiichi Rika Co., Ltd.), and color of this coating film was recorded as an initial state (sample). It is to be noted that, for a sample in which no coloration was observed, symbol "-" was shown in the table.

The sample was allowed to stand at room temperature for 30 minutes or more and then placed on a table, and water was sprayed on the sample. Thereafter, final color, the degree of hue change (color difference) and time until color oozed out and changed to the final color were recorded and described in Tables 1 to 4.

Color Difference (Degree of Hue Change)

Evaluation criteria of the hue change are as follows.

A: A very clear difference in hue is observed before and after spraying

B: A clear difference in hue is observed before and after spraying

C: A slight difference in hue is observed before and after spraying

D: No difference in hue is observed before and after spraying

Color Bleeding

After color of the sample changed to the final color, the water-applied sample was vertically leaned from a table, and color bleeding associated with moisture dripping was recorded. When the color oozes out due to water, application pattern of the wet indicator applied to a diaper collapses and visibility deteriorates. Therefore, it is preferable as the composition for wet indicator when the color bleeding is less. The evaluation criteria are as follows.

A: No color bleeding is observed

B: Slight color bleeding is observed, but shape of the applied portion is retained C: Color bleeding is observed, but shape of the applied portion is retained D: Color bleeding is observed, and shape of the applied portion is lost and not retained Time Until it Became Final Color Time from spraying of water until it became the final color was measured and described in Tables 1 to 4. It is to be noted that, for compositions in which no color difference was observed, symbol "-" was shown in the table.

TABLE 1

| | | Examples | | | | | | |
|---|---|---|---|---|---|---|---|---|
| | | 1 | 2 | 3 | 4 | 5 | 6 | 7 |
| Component composition | | | | | | | | |
| Hydrocarbon oil | Paraffin oil (liquid paraffin) | 66 | 8 | 20 | 0 | 0 | 83 | 81 |
| | Paraffin oil (KP-68) | 0 | 0 | 0 | 0 | 0 | 0 | 0 |
| | Paraffin oil (PW-32) | 0 | 0 | 0 | 63 | 34 | 0 | 0 |
| | Naphthene oil (KN4010) | 0 | 0 | 0 | 0 | 0 | 0 | 0 |
| Colorant | pH Indicator (bromocresol green) | 0 | 0 | 0 | 0 | 0 | 2 | 0 |
| | Leuco dye (crystal violet lactone) | 1 | 2 | 0 | 0.4 | 1 | 0 | 2 |
| | Leuco dye (Blue 1) | 0 | 0 | 0 | 0 | 0 | 0 | 0 |
| | Leuco dye (Blue 203) | 0 | 0 | 2 | 0 | 0 | 0 | 0 |
| Surfactant | Anionic (Na dodecylbenzene sulfonate) | 11 | 5 | 11 | 8 | 22 | 11 | 11 |
| | Anionic (Na dioctyl sulfosuccinate) | 0 | 0 | 0 | 0 | 0 | 0 | 0 |
| | Nonionic (AQ250) | 0 | 0 | 0 | 0 | 0 | 0 | 0 |
| Saturated fatty acid | 16-Hydroxyhexadecanoic acid | 0 | 0 | 0 | 0 | 0 | 0 | 0 |
| | Mg stearate | 0 | 0 | 0 | 0 | 0 | 0 | 0 |
| | 12-Hydroxystearic acid | 22 | 84 | 67 | 28 | 43 | 3 | 6 |
| | Na stearate | 0 | 0 | 0 | 0 | 0 | 0 | 0 |
| Tackifier resin | Hydrogenated gum rosin (RHR-101HK) | 11 | 5 | 10 | 9 | 9 | 10 | 10 |
| | Hydrogenated rosin (AX-E) | 0 | 0 | 0 | 0 | 0 | 0 | 0 |
| | Hydrogenated hydrocarbon (HD-1100) | 0 | 0 | 0 | 0 | 0 | 0 | 0 |
| | Hydrogenated hydrocarbon (P100) | 0 | 0 | 0 | 0 | 0 | 0 | 0 |
| | Hydrogenated hydrocarbon (ECR5400) | 0 | 0 | 0 | 20 | 45 | 0 | 0 |
| | Hydrogenated hydrocarbon (FTR-6100) | 0 | 0 | 0 | 0 | 0 | 0 | 0 |
| | Total | 111 | 104 | 110 | 129 | 154 | 110 | 110 |
| Composition applied sample | | | | | | | | |
| Performance evaluation results | Appearance (presence or absence of oily gel) | Presence of gel | Presence of gel | Presence of gel | Presence of gel | Presence of gel | Presence of gel | Presence of gel |
| | Appearance (hardness of composition for indicator) | Hard | Hard | Hard | Very hard | Very hard | Very soft | Soft |
| | Phase separation (100° C. for 24 hours) | A | C | A | A | A | A | A |
| | Odor | A | A | A | A | A | B | A |
| | Initial hue | — | Light blue | Light blue | — | — | Yellow | — |
| | Hue (final color) after water wetting | Blue | Dark blue | Dark blue | Blue | Blue | Blue | Blue |
| | Color difference | A | A | A | A | A | A | B |
| | Color bleeding | B | A | A | A | A | B | B |
| | Time until discoloration | Immediate | Immediate | Immediate | Immediate | Immediate | Immediate | Immediate |

TABLE 2

| | | Examples | | | | | | |
|---|---|---|---|---|---|---|---|---|
| | | 8 | 9 | 10 | 11 | 12 | 13 | 14 |
| Component composition | | | | | | | | |
| Hydrocarbon oil | Paraffin oil (liquid paraffin) | 0 | 0 | 0 | 0 | 0 | 0 | 0 |
| | Paraffin oil (KP-68) | 0 | 0 | 66 | 57 | 74 | 69 | 69 |
| | Paraffin oil (PW-32) | 67 | 0 | 0 | 0 | 0 | 0 | 0 |
| | Naphthene oil (KN4010) | 0 | 63 | 0 | 0 | 0 | 0 | 0 |
| Colorant | pH Indicator (bromocresol green) | 0 | 0 | 0 | 0 | 0 | 0 | 1 |
| | Leuco dye (crystal violet lactone) | 0.1 | 3 | 1 | 1 | 1 | 0 | 0 |
| | Leuco dye (Blue 1) | 0 | 0 | 0 | 0 | 0 | 1 | 0 |
| | Leuco dye (Blue 203) | 0 | 0 | 0 | 0 | 0 | 0 | 0 |
| Surfactant | Anionic (Na dodecylbenzene sulfonate) | 11 | 11 | 11 | 14 | 4 | 0 | 0 |
| | Anionic (Na dioctyl sulfosuccinate) | 0 | 0 | 0 | 0 | 0 | 10 | 0 |
| | Nonionic (AQ250) | 0 | 0 | 0 | 0 | 0 | 0 | 10 |
| Saturated fatty acid | 16-Hydroxyhexadecanoic acid | 0 | 0 | 0 | 0 | 0 | 0 | 0 |
| | Mg stearate | 0 | 0 | 0 | 0 | 0 | 0 | 0 |
| | 12-Hydroxystearic acid | 22 | 22 | 22 | 28 | 21 | 20 | 20 |
| | Na stearate | 0 | 0 | 0 | 0 | 0 | 0 | 0 |
| Tackifier resin | Hydrogenated gum rosin (RHR-101HK) | 10 | 10 | 0 | 0 | 4 | 0 | 0 |
| | Hydrogenated rosin (AX-E) | 0 | 0 | 10 | 0 | 0 | 0 | 0 |
| | Hydrogenated hydrocarbon (HD-1100) | 0 | 0 | 0 | 0 | 0 | 0 | 0 |
| | Hydrogenated hydrocarbon (P100) | 0 | 0 | 0 | 0 | 0 | 0 | 0 |
| | Hydrogenated hydrocarbon (ECR5400) | 0 | 0 | 0 | 0 | 0 | 0 | 0 |
| | Hydrogenated hydrocarbon (FTR-6100) | 0 | 0 | 0 | 28 | 0 | 0 | 0 |
| | Total | 110 | 110 | 110 | 128 | 104 | 100 | 100 |
| Composition applied sample | | | | | | | | |
| Performance evaluation results | Appearance (presence or absence of oily gel) | Presence of gel | Presence of gel | Presence of gel | Presence of gel | Presence of gel | Presence of gel | Presence of gel |
| | Appearance (hardness of composition for indicator) | Soft | Soft | Soft | Hard | Soft | Soft | Soft |
| | Phase separation (100° C. for 24 hours) | A | A | A | B | B | B | C |
| | Odor | A | A | A | A | A | A | B |
| | Initial hue | — | — | — | — | — | — | Yellow |
| | Hue (final color) after water wetting | Light Blue | Dark blue | Dark blue | Dark blue | Dark blue | Blue | Light blue |
| | Color difference | B | A | A | A | A | B | B |
| | Color bleeding | B | B | B | A | B | B | B |
| | Time until discoloration | Immediate | Immediate | Immediate | Immediate | Immediate | Immediate | Immediate |

TABLE 3

| | | Examples | | | | | | |
|---|---|---|---|---|---|---|---|---|
| | | 15 | 16 | 17 | 18 | 19 | 20 | 21 |
| Component composition | | | | | | | | |
| Hydrocarbon oil | Paraffin oil (liquid paraffin) | 0 | 0 | 0 | 64 | 64 | 0 | 53 |
| | Paraffin oil (KP-68) | 54 | 51 | 0 | 0 | 0 | 43 | 0 |
| | Paraffin oil (PW-32) | 0 | 0 | 40 | 0 | 0 | 0 | 0 |
| | Naphthene oil (KN4010) | 0 | 0 | 0 | 0 | 0 | 0 | 0 |
| Colorant | pH Indicator (bromocresol green) | 0 | 0 | 0 | 2 | 2 | 0 | 0 |
| | Leuco dye (crystal violet lactone) | 1 | 0 | 0 | 0 | 0 | 1 | 2 |
| | Leuco dye (Blue 1) | 0 | 0.4 | 0 | 0 | 0 | 0 | 0 |
| | Leuco dye (Blue 203) | 0 | 0 | 0.2 | 0 | 0 | 0 | 0 |
| Surfactant | Anionic (Na dodecylbenzene sulfonate) | 10 | 17 | 17 | 11 | 11 | 13 | 7 |
| | Anionic (Na dioctyl sulfosuccinate) | 0 | 0 | 0 | 0 | 0 | 0 | 0 |
| | Nonionic (AQ250) | 0 | 0 | 0 | 0 | 0 | 0 | 0 |

TABLE 3-continued

| | | Examples | | | | | | |
|---|---|---|---|---|---|---|---|---|
| | | 15 | 16 | 17 | 18 | 19 | 20 | 21 |
| Saturated fatty acid | 16-Hydroxyhexadecanoic acid | 0 | 0 | 0 | 22 | 0 | 0 | 0 |
| | Mg stearate | 0 | 0 | 0 | 0 | 22 | 0 | 0 |
| | 12-Hydroxystearic acid | 34 | 0 | 42 | 0 | 0 | 43 | 0 |
| | Na stearate | 0 | 32 | 0 | 0 | 0 | 0 | 39 |
| Tackifier resin | Hydrogenated gum rosin (RHR-101HK) | 12 | 8 | 10 | 10 | 10 | 9 | 6 |
| | Hydrogenated rosin (AX-E) | 0 | 0 | 0 | 0 | 0 | 0 | 0 |
| | Hydrogenated hydrocarbon (HD-1100) | 30 | 45 | 0 | 0 | 0 | 45 | 35 |
| | Hydrogenated hydrocarbon (P100) | 0 | 0 | 0 | 0 | 0 | 0 | 0 |
| | Hydrogenated hydrocarbon (ECR5400) | 0 | 0 | 38 | 0 | 0 | 0 | 0 |
| | Hydrogenated hydrocarbon (FTR-6100) | 0 | 0 | 0 | 0 | 0 | 0 | 0 |
| | Total | 142 | 153 | 148 | 110 | 110 | 154 | 141 |
| Composition applied sample | | | | | | | | |
| Performance evaluation results | Appearance (presence or absence of oily gel) | Presence of gel | Presence of gel | Presence of gel | Presence of gel | Presence of gel | Presence of gel | Presence of gel |
| | Appearance (hardness of composition for indicator) | Hard | Hard | Very hard | Soft | Soft | Very hard | Hard |
| | Phase separation (100° C. for 24 hours) | A | B | A | A | A | A | B |
| | Odor | A | A | A | B | B | A | A |
| | Initial hue | — | Light brown | — | Yellow | Light green | — | Light blue |
| | Hue (final color) after water wetting | Dark blue | Dark blue | Blue | Light blue | Dark blue | Dark blue | Dark blue |
| | Color difference | A | A | B | B | A | A | A |
| | Color bleeding | A | A | A | B | B | A | A |
| | Time until discoloration | Immediate | Immediate | Immediate | Immediate | Immediate | Immediate | Immediate |

TABLE 4

| | | Comparative Example | | | | |
|---|---|---|---|---|---|---|
| | | 1 | 2 | 3 | 4 | 5 |
| Component composition | | | | | | |
| Hydrocarbon oil | Paraffin oil (liquid paraffin) | 0 | 87 | 76 | 86 | 3 |
| | Paraffin oil (KP-68) | 0 | 0 | 0 | 0 | 0 |
| | Paraffin oil (PW-32) | 0 | 0 | 0 | 0 | 0 |
| Colorant | pH Indicator (bromocresol green) | 6 | 2 | 2 | 0 | 0 |
| | Leuco dye (crystal violet lactone) | 0 | 0 | 0 | 2 | 1 |
| Surfactant | Anionic (Na dodecylbenzene sulfonate) | 31 | 11 | 0 | 10 | 0 |
| Saturated fatty acid | 12-Hydroxystearic acid | 63 | 0 | 22 | 1 | 93 |
| Tackifier resin | Hydrogenated gum rosin (RHR-101HK) | 68 | 10 | 10 | 11 | 3 |
| | Hydrogenated hydrocarbon (ECR5400) | 0 | 0 | 0 | 0 | 0 |
| | Total | 168 | 110 | 110 | 110 | 110 |
| Composition applied sample | | | | | | |
| Performance evaluation results | Appearance (presence or absence of oily gel) | Absence of gel | Absence of gel | Absence of gel | Absence of gel | Absence of gel |
| | Appearance (hardness of composition for indicator) | Liquid | Hard solid | Hard gel | Liquid | Solid |
| | Phase separation (100° C. for 24 hours) | A | A | A | B | D |
| | Odor | D | D | D | A | A |
| | Initial hue | Dark yellow | Yellow | Light yellow | — | — |
| | Hue (final color) after water wetting | Dark yellow | Yellow | Light yellow | — | — |
| | Color difference | D | D | D | D | D |
| | Color bleeding | D | A | B | D | A |
| | Time until discoloration | — | — | — | — | — |

As shown in Tables 1 to 3, in the compositions for wet indicator of Examples, the components are not separated, and a strong odor is not generated. Further, in the compositions for wet indicator of Examples, a change in color is clear, time from the initial stage to the final discoloration is short, and the color is not blurred.

On the other hand, in the compositions for wet indicator of Comparative Examples 1 to 5, there is no change between the initial hue and the hue after wetted with water, and thus they are not suitable for indicators. In Comparative Examples 1 to 3, an odor cannot be suppressed.

INDUSTRIAL APPLICABILITY

The composition for wet indicator of the present invention provides a wet indicator to be attached to an absorbent article such as a diaper or a napkin.

The invention claimed is:

1. A composition for a wetness indicator, the composition comprising:
   a hydrocarbon oil;
   at least one saturated fatty acid selected from saturated fatty acids having 16 or more carbon atoms and derivatives thereof; and
   a wet-sensitive colorant composition comprising a colorant and a surfactant, wherein:
      the at least one saturated fatty acid is present in an amount of from 2 to 85 parts by mass, based on 100 parts by mass of the total amount of the composition,
      the hydrocarbon oil and the at least one saturated fatty acid are in the form of a crosslinked gel,
      the colorant undergoes discoloration in the presence of protons, and
      the surfactant releases protons in the presence of water.

2. The composition of claim 1, wherein the at least one saturated fatty acid is selected from 12-hydroxystearic acid and metal salts of 12-hydroxystearic acid.

3. The composition of claim 1, wherein the colorant is a leuco dye.

4. The composition of claim 3, wherein the wet-sensitive colorant composition further comprises a pH indicator.

5. A wetness indicator having the composition of claim 1.

6. An absorbent article having the wetness indicator of claim 5.

7. The composition of claim 1, wherein the surfactant is a nonionic surfactant.

8. The composition of claim 1, wherein the surfactant is an anionic surfactant.

9. The composition of claim 8, wherein the anionic surfactant is a linear alkylbenzene sulfonate.

10. The composition of claim 1, wherein the hydrocarbon oil has a weight average molecular weight of from 200 to 2000.

11. The composition of claim 1, wherein the hydrocarbon oil is present in an amount of from 5 to 90 parts by mass, based on 100 parts by mass of the composition.

12. A composition for a wetness indicator, the composition comprising:
   a hydrocarbon oil;
   at least one saturated fatty acid selected from saturated fatty acids having 16 or more carbon atoms and derivatives thereof; and
   a wet-sensitive colorant composition comprising a leuco dye, wherein:
      the at least one saturated fatty acid is present in an amount of from 2 to 85 parts by mass, based on 100 parts by mass of the total amount of the composition, and
      the hydrocarbon oil and the at least one saturated fatty acid are in the form of a crosslinked gel.

13. The composition of claim 12, wherein the wet-sensitive colorant composition further comprises a pH indicator.

14. The composition of claim 12, wherein the wet-sensitive colorant composition further comprises a surfactant.

15. The composition of claim 14, wherein the surfactant is a nonionic surfactant.

16. The composition of claim 14, wherein the surfactant is an anionic surfactant.

17. The composition of claim 12, wherein the hydrocarbon oil is present in an amount of from 5 to 90 parts by mass, based on 100 parts by mass of the total amount of the composition.

18. The composition of claim 12, wherein the wet-sensitive colorant composition is present in an amount of from 0.05 to 5 parts by mass, based on 100 parts by mass of the total amount of the composition.

19. The composition of claim 12, further comprising a rosin-based tackifier resin.

* * * * *